United States Patent
Bieniarz et al.

(10) Patent No.: US 6,245,949 B1
(45) Date of Patent: Jun. 12, 2001

(54) SYNTHETIC METHOD FOR THE FLUOROMETHYLATION OF ALCOHOLS

(75) Inventors: Christopher Bieniarz, Highland Park; Kornepati V. Ramakrishna, Libertyville, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/587,414

(22) Filed: Jun. 1, 2000

(51) Int. Cl.[7] .............................. C07C 41/01; C07C 41/09
(52) U.S. Cl. ......................... 568/683; 568/684; 568/685
(58) Field of Search .................... 568/683, 684, 568/685

(56) References Cited

U.S. PATENT DOCUMENTS

| Re. 35,568 | | 7/1997 | Halpern et al. ................ 568/683 |
|---|---|---|---|
| 3,683,092 | * | 8/1972 | Regan et al. .................. 424/342 |
| 4,250,334 | * | 2/1981 | Coon et al. ................... 568/683 |
| 4,314,087 | * | 2/1982 | Radlick ........................ 568/842 |
| 4,469,898 | * | 9/1984 | Coon et al. ................... 568/683 |
| 4,847,427 | | 7/1989 | Nappa .......................... 568/615 |
| 4,874,901 | | 10/1989 | Halpern et al. ................ 568/683 |
| 4,996,371 | | 2/1991 | Halpern et al. ................ 568/683 |
| 5,705,710 | * | 1/1998 | Baker et al. ................... 568/683 |
| 5,789,630 | | 8/1998 | Baker et al. ................... 570/141 |
| 5,811,596 | * | 9/1998 | Kawai et al. .................. 568/683 |
| 5,886,239 | * | 3/1999 | Kudzma et al. ................ 568/684 |
| 5,969,193 | * | 10/1999 | Terrell ......................... 568/683 |
| 5,990,359 | * | 11/1999 | Ryan et al. .................... 568/683 |
| 6,100,434 | * | 8/2000 | Bieniarz et al. ................ 568/683 |

FOREIGN PATENT DOCUMENTS 0 042 412 * 12/1981 (EP) .

* cited by examiner

*Primary Examiner*—Johann Richter
(74) *Attorney, Agent, or Firm*—Brian R. Woodworth

(57) ABSTRACT

A method for fluoromethylating halogenated alcohols. The method includes the step of providing an alpha-halogenated alcohol of the formula $R^1C(CX_3)_2OH$, wherein $R^1$ is selected from the group consisting of hydrogen and alkyl groups. The alpha-halogenated alcohol is reacted with a first compound of the formula $CH_2(OR^2)_2$ in the presence of an acid catalyst to form an acetal. The resulting acetal is then chlorinated with a chlorinating agent to form a chloride compound of the formula $R^1C(CX_3)_2OCH_2Cl$. The chloride compound is then converted to a fluoride compound of the formula $R^1C(CX_3)_2OCH_2F$ using a fluorinating agent.

12 Claims, No Drawings

SYNTHETIC METHOD FOR THE FLUOROMETHYLATION OF ALCOHOLS

FIELD OF THE INVENTION

The present invention is directed to a method for fluoromethylation of halogenated alcohols. An alcohol is reacted with a dialkoxymethane under acidic conditions to yield an acetal, which then is fluorinated by reacting it with a Lewis acid and a fluorinating agent. The method produces fluorinated compounds in high yield, and may be carried out in a single vessel. Preferably, the method may be used to synthesize sevoflurane from hexafluoroisopropanol.

BACKGROUND OF THE INVENTION

Anesthetics belong to a class of biochemical depressant drugs which affect the vital functions of cells. Anesthetics generally produce analgesia, loss of consciousness, diminished reflex activity, and muscular relaxation, with minimal depression of the vital functions. Anesthetics may be gaseous (volatile) or fixed (non-volatile). Gaseous anesthetics are inhaled and enter the bloodstream through the lungs while fixed anesthetics are administrated parenterally or through the alimentary canal.

Many currently used gaseous anesthetics are halogenated compounds. These compounds tend to cause less metabolic disturbance and are less flammable than traditional gaseous anesthetic compounds such as ether and cyclopropane. Examples of halogenated anesthetic compounds include halothane ($CF_3CHBrCl$) and trichloroethylene ($Cl_2C=CHCl$) as well as halogenated ether compounds such as enflurane ($CHF_2OCF_2CHClF$), fluroxene ($CF_3CH_2OCH=CH_2$), methoxyflurane ($Cl_2CHCF_2OCH_3$), and isoflurane ($CF_3CHClOCHF_2$).

A particularly useful halogenated ether anesthetic is sevoflurane, $(CF_3)_2CHOCH_2F$, also known as 2-(fluoromethoxy)- 1,1,1,3,3,3,-hexafluoropropane or fluoromethyl-1,1,1,3.3,3-hexafluoro-2-propyl ether. Sevoflurane is today one of the most important and widely used general anesthetics. Sevoflurane combines various characteristics that are most desirable in an inhalation anesthetic, including the lowest blood/gas partition coefficient of 0.63, smooth induction and recovery from anesthesia, minimal irritation to the upper respiratory tract, low metabolic rate, and rapid elimination. In addition, sevoflurane is suitable for out-patient surgery use. Although sevoflurane's definitive mechanism of action has not been elucidated, it has recently been shown that sevoflurane interacts with nicotinic acetylcholine receptors by affecting the open and closed state of the ion channels at clinical and lower concentrations. Sevoflurane may also effect reversible modulation of GABA and glycine receptors. The above suggest that at least part of the anesthetic action of sevoflurane may be due to interactions between sevoflurane and specific voltage-gated ion channels.

The preparation of fluorinated compounds such as sevoflurane tends to be difficult because of the limited number of selective fluorination reactions available. Direct fluorination of organic compounds to replace hydrogen is statistical, non-selective, and generally accompanied by the formation of many side products. Hence, fluorinated compounds are usually prepared by first synthesizing a substituted organic intermediate. wherein the substituent group is at the site to be fluorinated, and then displacing the substituent group with a fluoride ion. Metal fluorides, for example, have been used to displace chlorine substituent groups.

Several synthetic routes to sevoflurane employ hexafluoroisopropyl alcohol (HFIP) as a starting material. For example, U.S. Pat. No. 3,683,092 discloses a method for synthesizing sevoflurane involving the methylation of hexafluoroisopropyl alcohol followed by fluorination with either (a) bromine trifluoride, or (b) chlorine gas, followed by potassium fluoride. U.S. Pat. No. 4,469,898 discloses a method for synthesizing sevoflurane which includes the mixing of hexafluoroisopropyl alcohol, formaldehyde, hydrogen fluoride, and a protonating, dehydrating and fluoride ion generating agent. U.S. Pat. No. 4,250,334 discloses a method for synthesizing sevoflurane by adding HFIP to a mixture of a stoichiometric excess of paraformaldehyde and hydrogen fluoride, plus sufficient sulfuric acid to sequester most of the water produced by the reaction. U.S. Pat. No. 4,314,087 discloses a method for synthesizing sevoflurane by reacting HFIP with hydrogen fluoride and a formaldehyde.

The routes disclosed in the referenced patents can result in unwanted by-products which may be difficult to separate from sevoflurane produced by the synthesis. Moreover, the use of corTosive materials in these synthetic routes requires specialized equipment and special handling precautions.

Other methods used to make hexafluoroisopropyl ethers include the conversion of 1,1,1,3,3,3-hexachloroisopropyl ethers to 1,1,1,3,3,3-hexafluoroisopropyl ethers. For example, methyl 1,1,1,3,3,3-hexachloroisopropyl ether and chloromethyl 1,1,1,3,3,3-hexachloroisopropyl ether can be converted to sevoflurane by reaction of each of the above compounds with bromine trifluoride. Hexafluoroisopropyl ethers also can be made by reacting each of these chlorinated compounds with hydrogen fluoride, followed by reaction with bromine trifluoride. U.S. Pat. No. 4,874,901 discloses a method for fluorinating halogenated ether compounds, wherein compounds such as sevoflurane can be prepared by reacting chloromethyl hexafluoroisopropyl ether with either potassium fluoride or sodium fluoride. However, the chlorine replacement methods are not desirable because large volumes of chloride are released in the synthetic process, the yields are low, and multiple chloro-fluoro intermediates are formed. The intermediates must be removed to obtain the final ether product, sevoflurane. The purification processes increase the difficulty and cost of synthesis of 1,1,1,3,3,3-hexafluoroisopropyl ethers by these methods.

Hexafluoropropanes alternatively have been synthesized from malononitrile in the presence of bromine trifluoride, as disclosed in U.S. Pat. Nos. 5,789,630 and 5,705,710.

Another potential route to sevoflurane is by fluorodecarboxylation. Patrick et al. *J Org. Chem.* 48, 4158–4159 (1983), reports that alkyl carboxylic acids can undergo fluorodecarboxylation with xenon difluoride ($XeF_2$) in the presence of hydrogen fluoride. Although the use of xenon difluoride on a small scale can be effective, the cost of xenon difluoride makes its use impractical on a large scale. Furthermore, when alkoxyacetic acids are fluorodecarboxylated with xenon difluoride, significant amounts of side products are formed. Replacement of a carboxylic acid group with a fluorine group has also been disclosed in U.S. Pat. No. 4,996,371 and in RE 35,568 which teach a reaction of hydrogenated aliphatic carboxylic acid compounds with bromine trifluoride; and in U.S. Pat. No. 4,847,427, which teaches a method for preparing fluorocarbon polyethers by neutralizing a perfluorinated carboxylic acid by heating with fluorine in the presence of metal fluoride to replace the carboxylic acid group.

While the above-discussed methods are useful for preparing certain fluorinated compounds, these methods can be complex, expensive, and often provide fluorinated products in low yield together with considerable amounts of side products. Hence there is a need for improved procedures for the preparation of fluorinated compounds.

SUMMARY OF THE INVENTION

The present invention is directed to a novel method for the fluoromethylation of alcohols. The method includes the steps of:

(a) reacting a halogenated alcohol with a dialkoxymethane of the general formula $CH_2(OR)_2$, wherein R is an alkyl group, an alkenyl group, or an alkynyl group, in the presence of an acid catalyst to form an acetal;

(b) chlorinating the acetal with a chlorinating agent to form a chloromethyl ether;

(c) converting the chloromethyl ether to a fluoride with a fluorinating agent in the presence of a solvent to form the desired fluorinated haloalcohol.

The present invention is further directed to a method for synthesizing sevoflurane including the steps of:

(a) reacting 1,1,1,3,3,3-hexafluoroisopropanol with $CH_2(OR^2)_2$ in the presence of an acid catalyst to form an acetal of the general formula $(CF_3)_2CHOCH_2OR^2$, wherein $R^2$ is an alkyl group, an alkenyl group, or an alkynyl group;

(b) chlorinating the acetal with a chlorinating agent in the presence of a first solvent to form sevochlorane (i.e., $(CF_3)_2CHOCH_2Cl$); and (c) converting the sevochlorane to sevoflurane with a fluorinating agent in the presence of a second solvent.

DETAILED DESCRIPTION OF THE INVENTION

As used herein, the term "alkyl" means straight or branched, saturated carbon chains.

As used herein, "sevochlorane" means a compound of the formula $(CF_3)_2CHOCH_2Cl$.

The method of the present invention can be performed in a single pot, although it will be appreciated that the described method can be practiced in multiple pots. A "single pot" process is a process that is performed in a single reaction vessel. It will be appreciated by those of ordinary skill that single pot processes provide certain advantages over multiple pot processes. For example, single pot processes require less handling and/or transfer of components, thereby reducing the risk of accident or mistake. Single pot processes also tend to be less expensive than multiple pot processes as a result of the reduction in handling and transfer of reaction ingredients.

In accordance with one aspect of the present invention, a halogenated alcohol, for example, a halogenated alcohol of the general formula $R^1C(CX_3)_2OH$ (where $R^1$ is selected from the group consisting of hydrogen alkyl groups, alkenyl groups and alkynyl groups and where X is selected from the group consisting of fluorine, bromine, chlorine, and iodine) is reacted with a dialkoxymethane of the general formula $CH_2(OR^2)_2$ (where $R^2$ is an alkyl group, alkenyl group or a alkynyl group and can be the same or different than $R^1$) under acidic conditions, e.g., in the presence of an acid catalyst, to form a mixed acetal of the general formula $R^1C(CX_3)_2OCH,OR^2$.

The acid catalyst used in this step of the reaction of the present invention can be a variety of known acid catalysts including, but not limited to, $ZnCl_2$, $AlCl_3$, $P_2O_5$, paratoluenesulfonic acid, $H_2SO_4$, silica gel, or montmorillonite.

An example of a halogenated alcohol that can be fluoromethylated in accordance with the method of the present invention is hexafluoroisopropanol (HFIP), although it will be appreciated that other halogenated alcohols can be used without departing from the intended spirit and scope of the invention. For example, other fluorinated, brominated, chlorinated, and iodinated alcohols can be fluoromethylated in accordance with the method. Further, the fluoromethylation method of the present invention can be used to fluoromethylate primary, secondary, and tertiary beta-halogenated alcohols.

Suitable dialkoxymethanes of the formula $CH_2(OR^2)_2$ include, but are not necessarily limited to, dimethoxymethane, dipropoxymethane, and dibutoxymethane.

The resulting mixed acetal, $R^1C(CX_3)_2OCH_2OR^2$, is then chlorinated with a chlorinating agent in the presence of a first solvent to form a chloromethyl ether of the general formula $R^1C(CX_3)_2OCH_2Cl$. Useful chlorinating agents include $AlCl_3$, HCl, and $PCl_5$. The first solvent can be a compound of the formula $HO-(CH_2CH_2O)_nH$, wherein n is an integer from one to twenty (inclusive), and preferably wherein n is an integer of from seven to ten (inclusive). In one embodiment of the method of the present invention, the first solvent is polyethylene glycol (PEG), preferably PEG 400, i.e., a polyethylene glycol having a molecular weight of approximately 400. Other possible first solvents include dimethyl formamide (DMF); n-methyl pyrrolidone (NMP); and dimethyl sulfoxide (DMSO). Persons of ordinary skill in the pertinent art will appreciate that alternative first solvents can be used in accordance with the method of the present invention without departing from the spirit and scope of the present invention.

The acid catalyst used in forming the acetal and the chlorinating agent can be, but need not be, the same compound. For example, both the acid catalyst and the chlorinating agent can be aluminum trichloride, $AlCl_3$. It will be appreciated that other compounds such as HCl can be used as both the acid catalyst and the chlorinating agent in accordance with the method of the present invention. In one embodiment of the method of the present invention, zinc dichloride is used as the acid catalyst in forming the acetal. Other acid catalysts can be used in connection with the method of the present invention, including, but not limited to, Lewis acids such as $ZnCl_2$, an acidic clay such as montmorillonite, and Bronsted acids such as HCl, para-toluene sulfonic acid, and $H_2SO_4$.

Thereafter, the resulting chloromethyl ether of the formula $R^1C(CX_3)_2OCH_2Cl$, is fluorinated with a fluorinating agent in a second solvent to form a fluorinated compound of the general formula $R^1C(CX_3)_2OCH_2F$. The fluorinating agent can be selected from a group of fluorinating agents that includes KF, NaF, CsF, $NaHF_2$, $KHF_2$. However, those of ordinary skill in the pertinent art may recognize that other fluorinating agents may be used in accordance with the present invention. Suitable second solvents include each of the above-referenced suitable first solvents. The first and second solvents can be the same or different. The second solvent may optionally include a co-solvent, e.g., water, present in an amount of 0.1% to 5% weight/weight relative to said third solvent.

The disclosed reaction can take place over a wide range of temperatures, for example from 0° C. to 150° C. In one embodiment, the reaction occurs at a temperature between 20° C. and 100° C. The temperature chosen may depend upon various factors known by those of ordinary skill in the art. For example, higher temperatures may be preferable when the reaction is carried out at a pH value within the range from 4 to 10, while the reaction will generally proceed satisfactorily at ambient temperature at a pH of about 10 or above.

The time required for the reaction will vary widely depending upon many factors, notably the nature of the substrates, the reaction temperature, the pH, and nature of the buffer or other medium used, especially the temperature and pH. However, within the preferred, above-identified pH and temperature ranges, a reaction period of from 5 minutes to 50 hours will normally suffice.

In another aspect of the present invention, sevoflurane is produced using the above-referenced reaction scheme. In this embodiment, 1,1,1,3,3,3-hexafluoroisopropanol is reacted with a compound of the general formula $CH_2(OR^2)_2$, in the presence of an acid catalyst to form an acetal, wherein $R^2$ is an alkyl group, an alkenyl group, or an alkynyl group. The resulting acetal is then chlorinated with a chlorinating agent in the presence of a first solvent to form sevochlorane which is fluorinated with a fluorinating agent in the presence of a second solvent to form sevoflurane.

Sevoflurane produced in accordance with the method of the present invention can be isolated from the resulting reaction mixture using known distillation techniques, e.g., flash distillation. In one embodiment of the present invention, sevoflurane is isolated from the products of the reaction by the addition of water into the resulting products. Sevoflurane is not soluble in water and therefore separates as a lower layer in the reaction vessel. In contrast, any impurities and solvents present in the products of the second reaction step are soluble in water and will therefore be present in the water in the reaction vessel. The sevoflurane can be separated from the water containing the dissolved impurities and solvents using known techniques.

It is contemplated that those skilled in the pertinent art may use other reaction conditions without departing from the intended spirit and scope of the present invention which is defined by the appended claims.

The present invention is further illustrated by the following examples which are presented for the purpose of demonstrating, but not limiting, the method of this invention. All analyses were conducted by gas chromatography. All percentages are in mole percent.

EXAMPLE 1

Methoxy-1,1,1,3,3,3-hexafluoroisopropoxymethane was synthesized in the following manner, according to Reaction Scheme I.

Reaction Scheme I

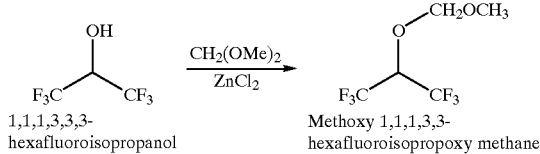

To an ice cold and well stirred suspension of $ZnCl_2$(41 g) (0.30 mole) in 1,1,1,3,3,3-hexafluoroisopropanol (31.5 mL) (0.31 mole), dimethoxymethane (24 mL) (0.30 mole) was added slowly over 5 minutes. The reaction mixture was brought up to room temperature in 1 hour and then was heated under reflux. After 6 hours of reflux, the contents of the reaction flask were distilled, leaving the solid residue in the flask. The distillate was washed with 2N NaOH (10×4), water (10 mL), brine (10 mL) and the bottom organic layer was separated and dried over anhydrous sodium sulfate and filtered to afford methoxy-1,1,1,3,3,3-hexafluoroisopropoxymethane (34 g, 55%).

EXAMPLE 2

Sevoflurane was synthesized in the following manner, according to Reaction Scheme II.

Reaction Scheme II

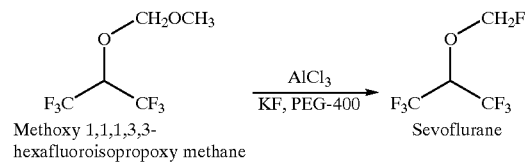

To methoxy-1,1,1,3,3,3-hexafluoroisopropoxymethane (3.57 g, 17 mmol), anhydrous $AlCl_3$ (2.25 g, 17 mmol) was added at room temperature and then the reaction flask was heated at 95° C. After 14 hours, the reaction mixture was cooled to room temperature and then PEG-400 (5.0 mL) and KF (1.97g 34 mmol) were added. The reaction mixture was then reheated to 95° C. After 18 hours, the reaction mixture was cooled to room temperature and diluted with 20 ml of water. The lower organic layer was separated and distilled to afford sevoflurane (2.4 g, 51%)

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the intended spirit and scope of the invention as defined in the appended claims.

What is claimed is:

1. A method for fluoromethylating halogenated alcohols, said method comprising the steps of:

providing a halogenated alcohol of the formula $R^1C(CX_3)_2OH$, wherein $R^1$ is selected from the group consisting of hydrogen, alkyl groups, alkenyl groups, and alkynyl groups, and wherein X is selected from the group consisting of fluorine, bromine, chlorine, and iodine;

reacting said halogenated alcohol with a dialkoxymethane of the formula $CH_2(OR^2)_2$ in the presence of an acid catalyst to form an acetal of the formula $R^1C(CX_3)_2OCH_2OR^2$, wherein $R^2$ is an alkyl group, an alkenyl group, or an alkynyl group;

chlorinating said acetal with a chlorinating agent to form a chloromethyl ether of the formula $R^1C(CX_3)_2OCH_2Cl$; and fluorinating said chloromethyl ether with a fluorinating agent to produce a fluoride compound of the formula $R^1C(CX_3)_2OCH_2F$.

2. A method in accordance with claim 1, wherein said acid catalyst and said chlorinating agent are the same compound.

3. A method in accordance with claim 1, wherein said fluorinating agent is selected from the group consisting of KF, NaF, CsF, $NaHF_2$, $KHF_2$.

4. A method in accordance with claim 3, wherein said fluorinating agent is KF.

5. A method in accordance with claim 1, wherein said chlorinating step is performed in the presence of a first solvent.

6. A method in accordance with claim 1, wherein said fluorinating step is performed in the presence of a second solvent.

7. A method in accordance with claim 1, wherein said dialkoxy methane is dimethoxymethane.

8. A method for fluoromethylating a halogenated alcohol, said method comprising the steps of:

reacting a halogenated alcohol with a dialkoxymethane of the formula $CH_2(OR)_2$ to form an acetal compound, wherein R is an alkyl group, an alkenyl group, or an alkynyl group;

chlorinating said acetal compound with a chlorinating agent to form a chloromethyl ether; and fluorinating said chloromethyl ether to a fluoride with a fluorinating agent to form a fluorinated haloalcohol.

9. A method in accordance with claim 8, wherein said halogenated alcohol is reacted with said dialkoxymethane in the presence of an acid catalyst.

10. A method in accordance with claim 8, wherein said acetal compound is chlorinated with a chlorinating agent in the presence of a first solvent.

11. A method in accordance with claim 8, wherein said chloromethyl ether is fluorinated in the presence of a second solvent.

12. A method for synthesizing sevoflurane, said method comprising the steps of:

reacting 1,1,1,3,3,3-hexafluoroisopropanol with a first compound of the formula $CH_2(OR^2)_2$ in the presence of an acid catalyst to form an acetal compound, wherein $R^2$ is an alkyl group, alkenyl group, or alkynyl group;

chlorinating said acetal compound with a chlorinating agent in the presence of a first solvent to form sevochlorane; and fluorinating sevochlorane produced by chlorinated said acetal compound to sevoflurane with a fluorinating agent in the presence of a second solvent.

* * * * *